(12) United States Patent
Selvam et al.

(10) Patent No.: US 11,844,906 B1
(45) Date of Patent: Dec. 19, 2023

(54) OXYGEN-AIR BLENDER FOR NEONATES

(71) Applicants: Selvaanish Selvam, Naperville, IL (US); Nathan Kostick, Saint Cloud, FL (US); Dhariyat Menendez, Mayfield Heights, OH (US); Amrish Selvam, Pittsburgh, PA (US)

(72) Inventors: Selvaanish Selvam, Naperville, IL (US); Nathan Kostick, Saint Cloud, FL (US); Dhariyat Menendez, Mayfield Heights, OH (US); Amrish Selvam, Pittsburgh, PA (US)

( * ) Notice: Subject to any disclaimer, the term of this patent is extended or adjusted under 35 U.S.C. 154(b) by 217 days.

(21) Appl. No.: 17/524,104

(22) Filed: Nov. 11, 2021

Related U.S. Application Data

(60) Provisional application No. 63/201,432, filed on Apr. 29, 2021.

(51) Int. Cl.
| | | |
|---|---|---|
| *A61M 16/00* | (2006.01) | |
| *A61M 16/12* | (2006.01) | |
| *A61M 16/20* | (2006.01) | |
| *A61M 16/10* | (2006.01) | |

(52) U.S. Cl.
CPC .......... *A61M 16/127* (2014.02); *A61M 16/20* (2013.01); *A61M 2016/1025* (2013.01); *A61M 2240/00* (2013.01)

(58) Field of Classification Search
CPC ............... A61M 16/127; A61M 16/20; A61M 2016/1025; A61M 2240/00
See application file for complete search history.

(56) References Cited

U.S. PATENT DOCUMENTS

| | | | | |
|---|---|---|---|---|
| 3,368,555 A | * | 2/1968 | Beasley | A61M 16/00 128/DIG. 10 |
| 4,440,164 A | | 4/1984 | Werjefelt | |
| 4,457,304 A | | 7/1984 | Molnar et al. | |
| 4,527,557 A | * | 7/1985 | DeVries | A61M 16/206 128/205.24 |

(Continued)

FOREIGN PATENT DOCUMENTS

| | | |
|---|---|---|
| BR | PI1002124 A2 | 3/2012 |
| EP | 1186315 A2 | 3/2002 |
| IN | 200954306 Y | 10/2007 |

OTHER PUBLICATIONS

Girish Deshpande, Gautham Oroskar, Derek Oswald, A Portable Handheld Oxygen Blender: A Novel Design to Reduce Early Oxygen Toxicity, ASME Article, Mar. 13, 2015, 6 pages, ASME, United States.

(Continued)

*Primary Examiner* — Steven O Douglas
(74) *Attorney, Agent, or Firm* — Kramer Law Clinic

(57) ABSTRACT

A portable oxygen-air blender including a gas distributor valve, a plurality of venturi valves, and an oxygen monitor. The gas distributor valve selectively routes the flow of oxygen from a compressed gas reservoir into one of several venturi valves to be blended with atmospheric air in a predetermined ratio. The blended oxygen-air mixture may be safely delivered to neonatal patients who require a specific concentration of oxygen to breathe. A monitoring system allows the user to verify concurrently that the patient is receiving the correct blend of oxygen and make adjustments to the patient's treatment.

3 Claims, 2 Drawing Sheets

(56) References Cited

U.S. PATENT DOCUMENTS

| | | | |
|---|---|---|---|
| 4,898,167 | A | 2/1990 | Pierce et al. |
| 6,253,764 | B1 | 7/2001 | Calluaud |
| 6,425,396 | B1 | 7/2002 | Adriance et al. |
| 6,708,688 | B1 | 3/2004 | Rubin |
| 8,181,250 | B2 | 5/2012 | Nelson |
| 9,255,721 | B2 | 2/2016 | Donohue |
| 10,335,569 | B2 | 7/2019 | Beard et al. |
| 10,946,163 | B2 | 3/2021 | Gillerman et al. |
| 10,953,187 | B2 | 3/2021 | Galbraith et al. |
| 10,953,189 | B2 | 3/2021 | Kertser |
| 10,954,893 | B2 | 3/2021 | Salley et al. |
| 2006/0207594 | A1* | 9/2006 | Stenzler .............. A61M 16/204 128/204.22 |
| 2008/0078385 | A1* | 4/2008 | Xiao .................... A61M 16/14 128/203.26 |
| 2009/0126734 | A1* | 5/2009 | Dunsmore ........ A61M 16/0858 128/204.23 |
| 2013/0192597 | A1 | 8/2013 | McKinnon et al. |
| 2017/0072159 | A1* | 3/2017 | Romano ........... A61M 16/0003 |
| 2018/0333555 | A1 | 11/2018 | Burke et al. |

OTHER PUBLICATIONS

Tri-Anim, Mixer, Air/Oxygen, MaxVenturi, High Flow, DISS Fittings, Pole Mount, Online product listing, United States.

* cited by examiner

OXYGEN-AIR BLENDER FOR NEONATES

TECHNICAL FIELD

The invention generally relates to concentrated oxygen delivery systems for patients, particularly oxygen delivery systems for neonates and infants.

BACKGROUND OF THE INVENTION

Neonatal infants ("neonates") facing a variety of health conditions cannot receive pure oxygen due to the harmful effects of free oxygen radicals. High concentrations of oxygen can lead to detrimental health effects that include organ failure and other developmental issues. These effects can be mitigated by administering the neonates a blend of oxygen and atmospheric air; however, there does not exist an adequate solution for transporting patients while they are receiving a blended gas. Furthermore, access to blended gases can be limited in transport and emergency situations because mobile facilities typically do not carry the required equipment. It is common for ambulances to only have compressed oxygen available. A transportable solution is needed to aid those patients who require an air-oxygen blend even outside of a hospital setting. The solution must be able to produce an air-oxygen blend using only a compressed oxygen source.

Various forms of gas blenders exist in the prior art, but these solutions commonly rely on additional gas sources, which are not readily available during transport. U.S. Pat. No. 8,181,650 to Nelson et al. describes a medical treatment respiratory apparatus having an oxygen inlet port and a medicant device port, which can be used to supply a patient with blended medicant gas. Such a gas blender is not suitable for use with neonates because the patient may still be exposed to concentrations of oxygen that are dangerously high.

Likewise, U.S. Pat. No. 4,898,167 to Pierce et al. provides for an emergency portable ventilator system to supply a patient with ambient air that is supplemented by an oxygen supply. However, for neonates, this device also presents a hazard because the flow of oxygen to the patient is governed by the rescuer's control over the oxygen reservoir. In an emergency situation, where the patient requires a specific concentration of oxygen, this device cannot control the concentration of gasses that are delivered to the patient.

As such, there is a need for an oxygen-air blender that is portable, does not require an external supply of inert gas, and that is suited for use on neonates by safely limiting the flow of oxygen to the patient.

BRIEF SUMMARY OF THE INVENTION

It is therefore an object of the present invention to provide for a portable blended gas delivery system, which draws in atmospheric air to blend with a compressed gas.

It is a further object of the present invention to provide for a portable blended gas delivery system which achieves the above object and which is also suited for use in the field by requiring minimal preparation or equipment.

It is yet another object of the present invention to provide for a blended gas delivery system which achieves the above objects and which also provides enhanced safety by supplying a gas blend in one of several predetermined ratios.

The invention achieves the above objects, and other objects and advantages which will become apparent from the description which follows, by providing a portable blended gas delivery system for patients using a gas distributor valve having a plurality of nozzles. Connected to the distributor valve is a means for removably coupling the delivery system to a compressed gas reservoir. A plurality of venturi valves, each having an inlet path and outlet path for the flow of gasses, are connected to the corresponding nozzles of the distributor valve. The distributor valve has a means for opening and closing the nozzles individually to direct a compressed gas through one of the nozzles into the inlet path of a connected venturi valve. An exhaust manifold having a plurality of inlet paths and an outlet path is provided, wherein every inlet path of the manifold is connected to the outlet path of the corresponding venturi. Connected to the outlet path of the exhaust manifold is a monitoring port which allows the user to monitor the gas concentration within the manifold. Also connected to the monitoring port is a means for removably coupling the delivery system to a patient.

In the preferred embodiments of the invention, the portable blended gas delivery system is provided with three venturi valves to selectively blend oxygen in concentrations of 50%, 65%, and 80% respectively. In an alternate embodiment, a bypass conduit may be provided to connect one of the nozzles of the gas distributor valve to one of the inlet paths of the exhaust manifold to bypass the venturi valves and provide the patient with undiluted oxygen.

DETAILED DESCRIPTION OF THE PREFERRED EMBODIMENTS

Figure 1:
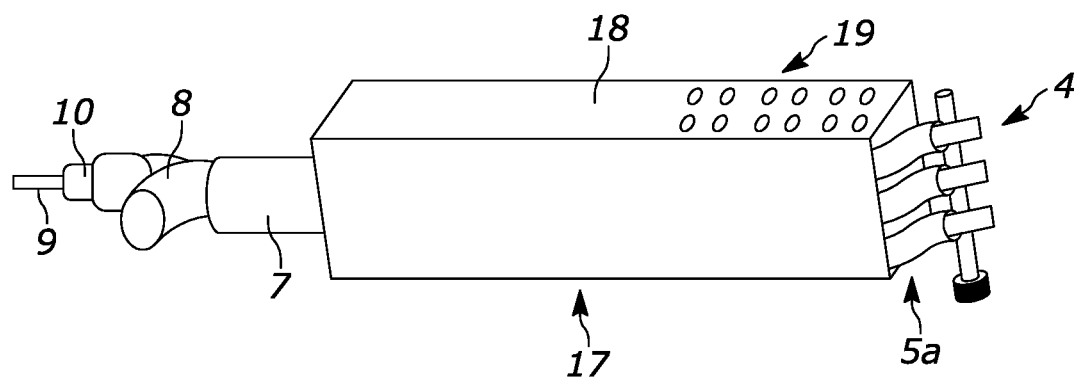
FIG. 1 is an isometric projection of the oxygen-air blender showing the gas distributor valve, exterior housing, vent holes, exhaust manifold, monitoring port, and delivery nozzle.
Figure 2:
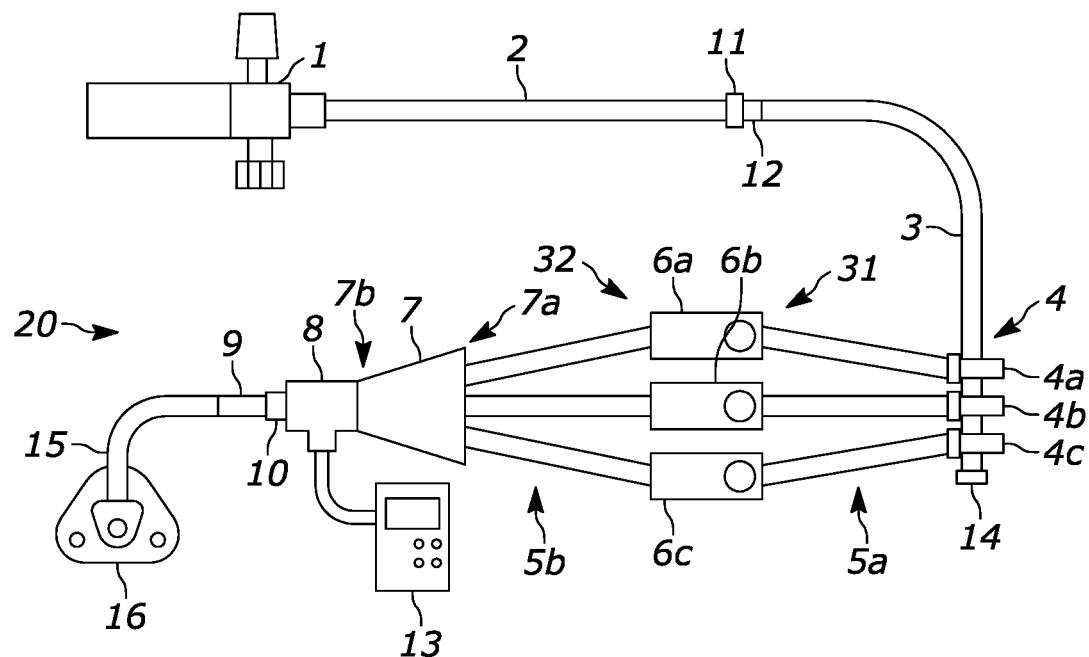
FIG. 2 is an elevational view of the oxygen-air blender removed from the exterior housing to show the venturi valves.
Figure 3:
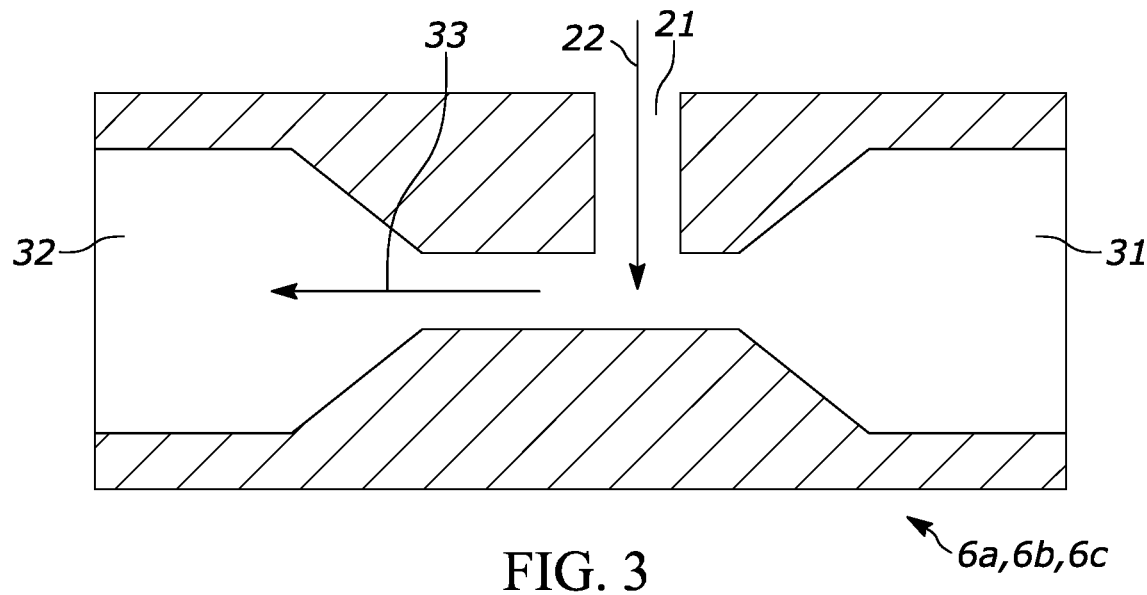
FIG. 3 is an elevational schematic representation of an exemplary venturi valve showing the inlet path, outlet path, and atmospheric air inlet.

A portable oxygen-air blender in accordance with the principles of the invention is generally indicated at reference numeral 20 in the various Figures of the attached drawings wherein numbered elements in the figures correspond to like numbered elements herein.

A medical oxygen flowmeter 1 screws onto an outlet of an oxygen tank to provide a flow of concentrated oxygen into an oxygen delivery hose 2. In the preferred embodiment, the oxygen delivery hose 2 is a Viair 92804 18 inch Stainless Steel Braided leader hose with check valve, Mfr. model No. 92791 (Viair Corp., Irvine CA). A flexible oxygen delivery tube 3 connects the oxygen delivery hose 2 to a gas distributor valve 4 to provide a flow of oxygen into the distributor valve 4. The connection between the oxygen delivery hose 2 and the flexible oxygen delivery tube 3 is made with a male hose connector 11 and a barbed hose fitting 12, which are threaded together. In the preferred embodiment, the flexible oxygen delivery tube 3 has an inner diameter of ¼ inches and an outer diameter of ⅜ inches. The male hose connector 11 is a ⅜ inch male connector metal pipe fitting, Mfr. model No. 6MSC6N-B (Parker Hannafin, Huntsville, AL). The barbed hose fitting 12 is a Seafit brass male pipe to hose NPT 3/8 in. x ⅛ barb fitting, Mfr. part No. 1859248 (West Marine Inc., Watsonville CA).

The gas distributor valve 4 includes a plurality of nozzles (preferably three) indicated generally at 4a, 4b, and 4c. The nozzles 4a, 4b, and 4c may be individually opened or closed by any conventional mechanism known to one skilled in the art, including but not limited to a ball valve, gate valve, pinch valve, needle valve, butterfly valve, globe valve, solenoid valve, plug, or cap. The nozzles 4a, 4b, and 4c each connect to a corresponding venturi valve 6a, 6b, and 6c via a plurality of oxygen interconnect hoses, indicated generally at 5a. Each of the venturi valves 6a, 6b, and 6c has an inlet path 31 and an outlet path 32, wherein the inlet path 31 of each venturi valve is connected to a corresponding one of the nozzles 4a, 4b, or 4c for allowing oxygen to pass through the venturi valve. Any nozzle which is not connected to a corresponding one of the oxygen interconnect hoses 5a may be sealed shut using a plug or screw-on cap 14. The oxygen interconnect hoses 5a each preferably have inner and outer diameters the same as the flexible oxygen delivery tube 3. Additionally, each of the venturi valves 6a, 6b, and 6c includes an atmospheric air inlet path 21 to intake air from the surrounding environment, the path of the air shown generally at 22, and blend the atmospheric air with pure oxygen in a predetermined ratio using the venturi effect. The path of the blended oxygen-air mixture as it exits through the outlet path 32 is shown generally at 33. The concentration of oxygen in the blended oxygen-air mixture depends on the diameter of the inlet path 31 and the internal configuration of the venturi valve. In the preferred embodiment, venturi valve 6a is an Air-Vac Model No. UV143H, venturi valve 6b is an Air-Vac Model No. AVR093H, and venturi valve 6c is an Air-Vac Model No. AVR062M (Air-Vac Engineering Co., Seymore CT). The venturi valves 6a, 6b, and 6c generate an oxygen-air blend having oxygen concentrations of 80%, 65%, and 50% respectively. Because the gas distributor valve 4 is configured to open only one of the nozzles 4a, 4b, and 4c at a given time, the flow of oxygen into one of the venturi valves 6a, 6b, and 6c produces a stream of blended gas in a ratio determined by the venturi valve that is selected. In the preferred embodiment, the venturi valves 6a, 6b, and 6c are held within a substantially rectangular exterior housing 17 having a top surface 18 with a plurality of ventilation holes 19 to facilitate the flow of atmospheric air into the venturi valves 6a, 6b, and 6c.

An exhaust manifold 7 has a plurality of inlet paths 7a that connect to the corresponding outlet paths 32 of the venturi valves 6a, 6b, and 6c by means of a plurality of blended gas interconnect hoses, indicated generally at 5b. Inside the exhaust manifold 7, a single outlet path 7b congregates the blended gas interconnect hoses 5b to direct the oxygen-air mixture into a monitoring port 8. A monitoring device 13 is connected to the monitoring port 8 to provide the user with a readout of the current oxygen concentration in the oxygen-air blend. In the preferred embodiment, the exhaust manifold 7 consists of a PVC pipe having an inner diameter of 1 inch, outer diameter of 1 and 5/16 inches, and length of 3 inches. The monitoring port 8 is a Mueller Proline ½ inch by ½ inch diameter Black iron tee fitting, Mfr. model No. 70403 (Mueller Streamline Co, Collierville TN). The monitoring device is an Analytical Industries Inc. All-2000 M Oxygen Monitor (Analytical Industries Inc., Pomona CA). A nozzle connector 10 is mounted to the monitoring port 8 and a delivery nozzle 9 is removably connected to the nozzle connector 10. In the preferred embodiment, the nozzle connector 10 is an Everbilt brass pipe hex bushing ½ inch MIP x ⅛ inch FIP, Mfr. part No. 762 052 and the delivery nozzle 9 is a Everbilt flare union ½ inch FL x ½ inch MIP, Mfr. part No. 915 148 (Home Depot Product Authority LLC, Atlanta GA).

The delivery nozzle 9 is connected to an end of a delivery tube 15 through which the oxygen-air blend is delivered to a patient via a patient interface 16. The patient interface 16 may be any conventional mechanism for delivering a gas mixture to a patient known to one skilled in the art, including but not limited to a full face mask, nasal mask, or nasal cannula.

Figure 4:
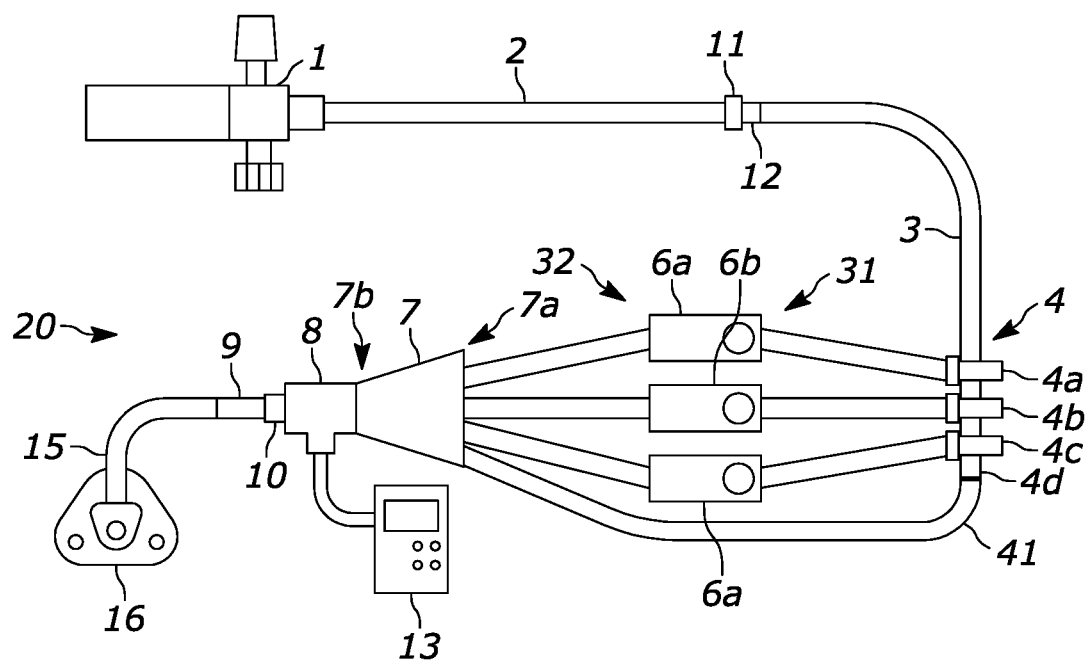
FIG. 4 is an elevational view of an alternate embodiment of the oxygen-air blender showing the addition of a bypass conduit connected in parallel with the venturi valves to deliver undiluted gas to the patient.

Referring now to FIG. 4, an alternate configuration of the oxygen-air blender is shown wherein a bypass conduit 41 is installed to connect nozzle 4d of the gas distributor valve 4 to an inlet path 7a of the exhaust manifold 7 to provide the patient with undiluted oxygen. The user changes the mode of operation of the oxygen-air blender in the field by first removing the plug or screw-on cap 14 from nozzle 4d, which was previously sealed to divert oxygen into nozzles 4a, 4b, and 4c. The user then connects an end of the bypass conduit 41 to the nozzle 4d and another end of the bypass conduit 41 to the corresponding inlet path 7a of exhaust manifold 7. This alternate configuration of the oxygen-air blender is suitable for delivering undiluted oxygen to adult and pediatric patients in the field who do not require a metered oxygen blend.

Those of ordinary skill in the art will conceive of other alternate embodiments of the invention upon reviewing this disclosure. Thus, the invention is not to be limited to the above description, but is to be determined in scope by the claims which follow.

What is claimed is:

1. A portable blended gas delivery system for patients, comprising:
   a gas distributor valve having a plurality of nozzles, the valve having means for opening and closing the nozzles individually;
   a plurality of venturi valves, each venturi valve having an inlet path and an outlet path, wherein the inlet path of each venturi is operatively connected to a corresponding one of the nozzles;
   an exhaust manifold having a plurality of inlet paths and an outlet path, wherein each of the inlet paths of the manifold is operatively connected to the outlet path of a corresponding one of the venturi valves;
   a monitoring port operatively connected to the outlet path of the exhaust manifold for monitoring the gas concentration within the manifold;
   a first means for removably coupling the delivery system to a compressed gas reservoir; and
   a second means for removably coupling the delivery system to a patient.

2. The portable blended gas delivery system of claim 1, wherein a bypass conduit connects one of the nozzles of the gas distributor valve to one of the inlet paths of the exhaust manifold to provide the patient with undiluted gas.

3. The portable blended gas delivery system of claim 1, wherein at least three venturi valves are configured to output a gas-air blend having gas concentrations of 50%, 65%, and 80% respectively.

* * * * *